United States Patent [19]

Joslyn

[11] Patent Number: 4,822,563

[45] Date of Patent: * Apr. 18, 1989

[54] METHOD FOR THE RECOVERY OF STERILANTS

[75] Inventor: Larry Joslyn, Macedon, N.Y.

[73] Assignee: Joslyn Value Corporation, Macedon, N.Y.

[*] Notice: The portion of the term of this patent subsequent to Sep. 13, 2005 has been disclaimed.

[21] Appl. No.: 112,333

[22] Filed: Oct. 26, 1987

[51] Int. Cl.⁴ .............................................. A61L 2/20
[52] U.S. Cl. ........................................ 422/31; 422/33; 422/34; 55/279
[58] Field of Search .................... 422/2, 31, 33, 34; 55/279

[56] References Cited

U.S. PATENT DOCUMENTS

| | | | |
|---|---|---|---|
| 3,549,312 | 5/1968 | Ernst | 422/31 |
| 4,555,251 | 11/1985 | Jonsson et al. | 422/34 |
| 4,770,851 | 9/1988 | Joslyn | 422/26 |

Primary Examiner—Barry S. Richman
Assistant Examiner—Lyle Alfandary Alexander
Attorney, Agent, or Firm—Martin Lukacher

[57] ABSTRACT

For safe removal and collection of chemical sterilants such as ethylene oxide from a sterilization process, steam or other substantially condesable, inert diluent gas is used to extract and to transport sterilant from the inside of sterilized materials and the sterilizing chamber into a collection tank. The sterilant and the condensable diluent are separated when the mixture is discharged from the sterilizing chamber such that virtually all of the sterilant can be collected as a liquid by compression and/or refrigeration at practical pressures and temperatures.

10 Claims, 1 Drawing Sheet

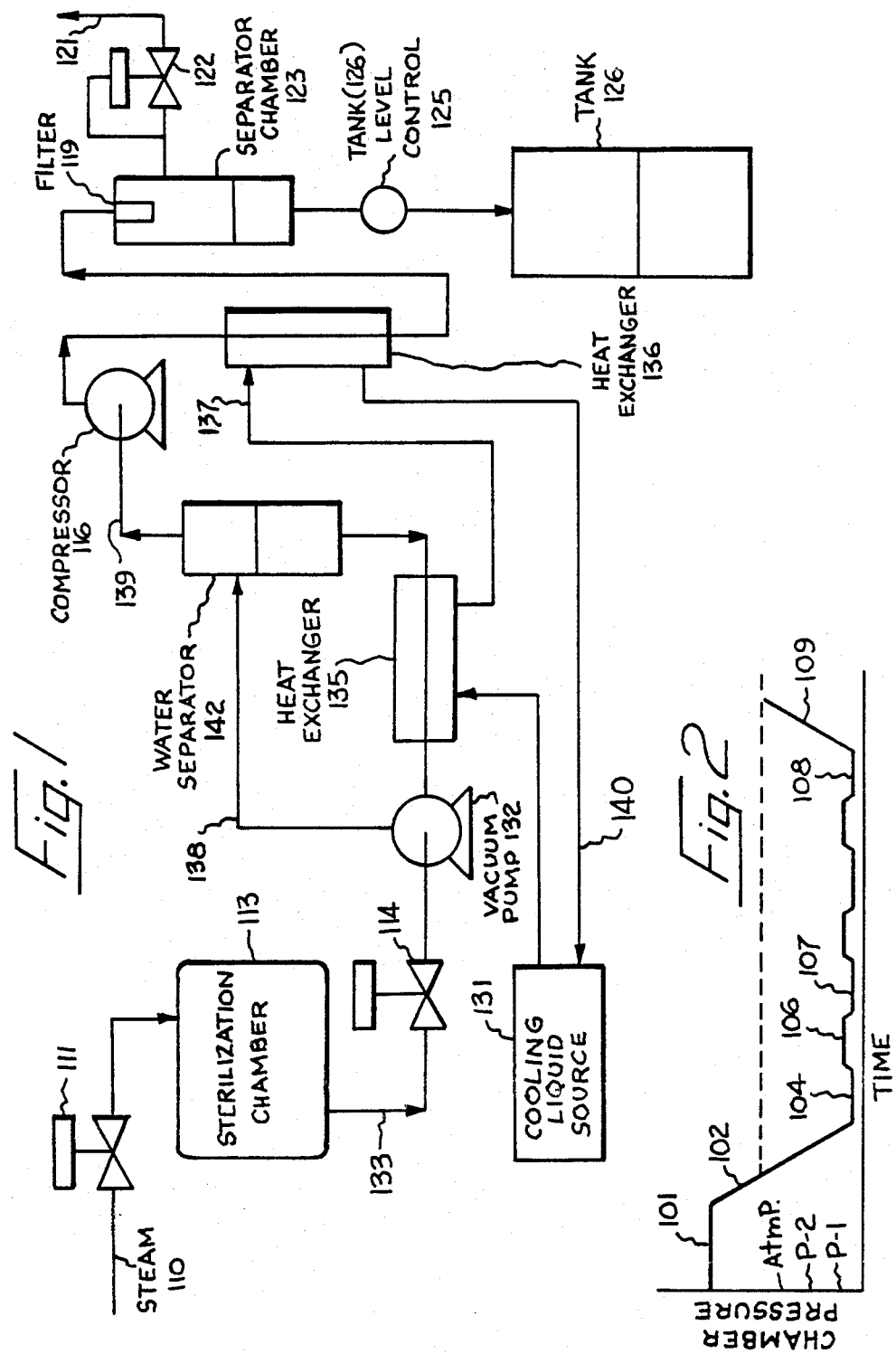

METHOD FOR THE RECOVERY OF STERILANTS

FIELD OF THE INVENTION

This invention relates to chemical sterilization and, more particularly, to a method for recovering chemical sterilant gases.

BACKGROUND

The most common forms of chemical sterilants used in hospitals and industrial sterilization facilities for sterilizing various plastic, fabric, paper, glass and metal articles consist of 100% ethylene oxide or a blend of 12% ethylene oxide and 88% by weight of dichlorodifluoromethane gas (e.g. "Freon 12" gas), the latter being an inert gas which reduces the flammability of ethylene oxide. There are concerns related to dumping of chemical sterilants such as ethylene oxide into the environment. Clouds of sterilant may drift into inhabited areas resulting in persons being exposed to toxic ethylene oxide. Additional concern has been expressed about the discharge of dichlorodifluoromethane gas into the environment as to its effect on the ozone layer of the upper atmosphere.

Current technology, as represented by U.S. Pat. No. 3,549,312, for recovering ethylene oxide sterilant gas consists of evacuating the sterilizing chamber and feeding the sterilant into a compressor and condenser to liquefy and collect the sterilant mixture in a holding tank. In this process, a large amount of the sterilant gas (approximately 10 to 15%) remains in the sterilizing chamber following evacuation. The water seal vacuum pumps typically employed on sterilizers are only capable of drawing vacuums from 1 to 2 pounds per square inch absolute (psia). Additionally, some items being sterilized, such as catheters and pouches, cannot withstand deep vacuums. Other types of high vacuum pumps are not used because the large quantities of moisture in the sterilizing processes contaminate the vacuum pumps and the vacuum pump seal oil. This can damage the pump, resulting in costly repairs and unreliable operation. Vacuum pump oil will also contaminate the sterilant being collected. For medical devices, this is unacceptable. The sterilant has to be kept pure.

In order to remove the remaining sterilant from a sterilizing chamber following the first evacuation, air is often pulsed into the chamber and the chamber is evacuated in a series of air pulses and vacuum steps to dilute the sterilant from the sterilized materials and the sterilizing chamber. The dilution with air makes it impractical to collect the remaining sterilant after the first vacuum which is drawn on the sterilizing chamber. The rest of the sterilant is generally discharged into the environment. In many locations throughout the world, however, government regulations prohibit such discharges. New York State, for instance, requires 99% reduction of the sterilant emission or the best available technology. To comply with allowable discharge limits, it is necessary to feed the discharge stream into a chemical scrubber which will remove the ethylene oxide. The Freon gas is still discharged into the environment with scrubber systems. Such discharges are not allowed in some locations in Europe, however, and it is expected that they will be prohibited in the United States in the future. The result is that even with very expensive recovery equipment the current technology does not solve the emission control problems.

There is additional concern about the potential of creating explosive conditions when air is used to dilute the ethylene oxide sterilant from the sterilized load and the sterilizing chamber. When air is pulsed into the sterilizing chamber, the ethylene oxide remaining in the load is compressed to a higher concentration locally within the load and mixed with air. This produces a hazardous condition because ethylene oxide is explosive when mixed with air. Thus, purging the system with air is not a good practice. Additionally, it is unsafe to attempt recovery of pure ethylene oxide from the mixture with air which would be discharged from the sterilizer.

Other non-condensing gaseous diluents such as nitrogen and carbon dioxide have been used to flush sterilant from the sterilizing chamber in order to prevent the formation of explosive mixtures. As with air, the partial pressure of the sterilant in these mixtures of non-condensing diluent gas and sterilant requires extremely cold temperatures in the condenser and high pressure compressor systems to collect the sterilant. The inefficiency of such systems makes it impractical to collect more than the sterilant discharged during the first vacuum drawn on the sterilizing chamber following sterilization.

The ideal way to handle chemicals which pollute the environment is to use the chemicals for the intended purpose and then recover them in a form that can be reused or converted into another useful product. Considering current and future discharge limits for ethylene oxide and Freon gas, an acceptable process must capture virtually all of the sterilant for reuse, conversion into another useful product or conversion into a nonpolluting chemical form. Additionally, the sterilant must be removed from the sterilizing chamber without creating a hazardous condition in either the sterilizing chamber or the collection apparatus.

It is an object of the present invention to provide a method for capturing virtually all of the sterilant gas from sterilizing chambers such that the sterilant can be reused or converted to a useful by-product or to a nonpolluting compound.

BRIEF SUMMARY OF THE INVENTION

It has been discovered, in accordance with the present invention, that an inert condensable gas such as steam can be used as a diluent to provide the safe removal of chemical sterilant gases, such as ethylene oxide, from a sterilizer and that the use of such a condensing diluent gas makes it possible to enhance the removal of sterilant from both the sterilized load, i.e., the materials or items being sterilized, and the sterilizing chamber and to capture virtually all of the sterilant gases such as ethylene oxide and any inert diluents such as Freon gas which are discharged from a sterilizing chamber.

In the method of the invention, a chemical sterilant gas is recovered from a sterilizing chamber by flushing the chamber with a condensable diluent gas and selectively condensing the effluent diluent gas to separate the sterilant gas from the diluent.

In a preferred embodiment of the invention a flammable sterilant gas is safely recovered from the chamber by (a) flushing the chamber with an inert, condensable diluent gas such as steam, then (b) raising the pressure in the chamber sufficiently to condense the dilutent gas, (c) reducing the pressure to vaporize the condensed dilutent gas and (d) repeating steps (a) through (c) until substantially all of the sterilant gas is recovered from the chamber. In more specific embodiments, the sterilant is ethylene oxide and is separated from the steam and condensed after removal from the chamber.

Other objects, features and advantages of the invention will become more apparent from a reading of the following description detailing methods in accordance with the invention and the presently preferred apparatus for use therewith which are shown in the accompanying drawings.

THE DRAWINGS

FIG. 1 is a schematic representation of an apparatus in which the method of the invention can be carried out.

FIG. 2 is a graphic representation of the method for chemical sterilant removal, with time on the horizontal axis and chamber pressure on the vertical axis.

DETAILED DESCRIPTION

The method of the invention is illustrated herein with specific reference to ethylene oxide as the chemical sterilant gas, steam as the condensable inert dilutent gas used for flushing the sterilizing chamber and dichlorodifluoromethane (e.g. Freon 12 gas) as the inert dilutent used to avoid the formation of explosive mixtures. It should be understood, however, that the method can, in accordance with the invention, be applied to other specific compounds. For example, the sterilant gas can be any such sterilant that is toxic, flammable or otherwise undesirable for release into the atmosphere. Such gases are referred to herein as chemical sterilants, to distinguish from environmentally harmless gases such as steam. Examples of chemical sterilant gases besides ethylene oxide include other alkylene oxides such as propylene oxide; aldehydes such as formaldehyde and glutaraldehyde; and chlorine containing gases such as chlorine dioxide. Likewise other condensable, inert gases besides steam could be used for flushing the sterilant from the chamber, including the inert halogenated hydrocarbon gases such as dichlorodifluoromethane. Steam is much preferred, however, for economy and because it can be vented to the atmosphere.

Referring to FIG. 1, the sterilizing chamber 113 containing a load to be sterilized is connected to devices to collect the discharge of sterilant gas from the sterilizer. For the purposes of this invention, only the means required for the collection of such discharge are shown connected to the sterilizing chamber.

A steam supply is connected to the sterilizing chamber 113 by a supply conduit 110 through a control valve 111. This arrangement provides a means for controlling the flow of steam into the sterilizing chamber 113.

A drain line 133 is connected to a vacuum pump 132 through control valve 114. The output of the vacuum pump is discharged into a water separator 142. The water separator removes the water from the vacuum pump discharge line 138 and returns the water through a heat exchanger 135 to the vacuum pump 132 to maintain the water seal required for the vacuum pump to operate. The heat exchanger removes heat from the seal water in order to condense out all or almost all of the steam which enters the vacuum pump from the sterilizing chamber and to maintain vacuum pump efficiency which is dependent on the water seal temperature.

A conduit 139 directs the discharge of gases from the separator 142 to a compressor 116 and a heat exchanger 136. The compressor increases the Pressure of the gases to above the liquefying pressure for the condensable gases at the temperature maintained in the heat exchanger. This results in liquefying of the gases which are condensable, e.g., the ethylene oxide sterilant gas and Freon gas, if the latter is present with the sterilant gas. The liquid and any non-condensable gases are fed through a coalescing filter 119 into a seParator chamber 123. It should be understood that gases are referred to herein as being "condensable" or "non-condensable" in a relative sense. Thus ethylene oxide and other commercially useful chemical sterilant gases, and condensable dilutents such as steam and Freon gas are condensable at commercially practicable pressures and termperatures. However, air and gases of similar vapor pressure are called non-condensable gases herein, since they do not condense at pressures and temperatures that are practical in commercial sterilizing systems. The coalescing filter causes the liquid (e.g., ethylene oxide and Freon 12 liquid) to separate from non-condensing gases (air) and the liquid is collected at the bottom of the separator chamber as shown at 124. The liquid is discharged from the separator chamber 123, through a liquid level control 125, to a collection tank 126 for reuse. The liquid level control allows only liquid to pass into the collection tank and the non-condensable gases remain in the separator 123.

A pressure regulator 122 is connected to the liquid separator 123. The pressure regulator regulates the pressure in the separator such that when the pressure of the non-condensable gas exceeds a level which would damage the compressor or significantly exceeds the liquefying pressure of the sterilant to be collected the regulator vents the non-condensable gases through conduit 121.

A refrigeration unit 131 provides a cooling liquid source to support the cooling heat exchanger 135 used in conjunction with the vacuum pump 132 and the liquefying heat exchanger 136 used in conjunction with the compressor 116.

Operation of the herein described apparatus to remove sterilant from the load (items which have been sterilized) and the sterilizing chamber and to capture this sterilant will be apparent from FIG. 2 which diagrams the pressure in the sterilizing chamber during the sterilant removal period.

During a sterilization process using a chemical sterilant gas such as ethylene oxide, the pressure in the sterilizing chamber can be at atmospheric or subatmospheric pressure, but advantageously is at a superatmospheric pressure e.g., 20 to 23 psia during the sterilizing exposure time at around 130° F. (54.4° C.) as shown at 101. At the end of the exposure time, e.g. 2 to 24 hours, the sterilizing chamber is evacuated as shown at 102. Referring to FIG. 1, this is accomplished by opening the vacuum control valve 114, turning on the vacuum pump 132 and compressor 116 and reducing the pressure in chamber 113, for example, to around 1-2 psia. The sterilant gas removed from the sterilizing chamber passes through the vacuum pump and into the water separator 142. The water separator removes the vacuum pump seal water from the sterilant gas at the discharge from the vacuum pump. Additionally, steam from the sterilizing chamber is condensed in the cold vacuum pump seal water. The sterilant exiting the separator enters the compressor 116, where it is compressed, and then passes into the cooling heat exchanger 136. At a given pressure relative to the temperature of the heat exchanger, for example, at 0 to 20° C. and a pressure at least 85 psia., for ethylene oxide, the sterilant is condensed into the liquid state. The liquid passes through the coalescing filter 119 into the liquid separator 123 to the liquid level control valve 125 which controls the level in the separator 123, and into collection tank 126 when the level in the separator exceeds a given level.

It should be appreciated that the gases discharged from the sterilizing chamber may not all be condensable. For instance, in some sterilization processes the air is not completely removed prior to the introduction of the sterilant or leaks in the sterilizing chamber may introduce air into the system when the chamber is at subatmospheric pressure. When these non-condensable gases, such as air, pass through the coalescing filter 119, liquid (the liquefied ethylene oxide sterilant) drops to the bottom 124 of the separator 123 and a head space consisting of the non-condensable gases forms in the separator. As the non-condensable gas accumulates, the pressure in the separator increases above the pressure required to condense the sterilant at the existing temperature. At a selected pressure above the condensing pressure, the non-condensing gases such as air are vented out of the separator through the pressure regulator 122. The non-condensable gases with a small amount of the sterilant gas exiting the discharge conduit 121 is vented into the atmosphere or into a small scrubber system to capture any trace quantities of ethylene oxide.

In systems where the non-condensable gases are removed from the sterilizing chamber prior to the admission of sterilant and the system is leak tight, there are no discharges from the pressure regulator. The majority of the sterilant is removed from the sterilizing chamber during the evacuation period shown at 102 of FIG. 2. There is, however, typically 8% to 15% of the sterilant in the sterilizing chamber, in the load voids and dissolved in the load following the first evacuation period. Referring to FIG. 2, the remaining sterilant is efficiently removed from the load and the sterilizing chamber by using a plurality of flush periods and pressure pulses with a condensable gas such as steam. At a given vacuum level (P-1), such as 1 to 2 psia, steam is admitted to the sterilizing chamber at a rate equal to the vacuum discharge capacity as shown at 104. The simultaneous flow of steam into the chamber and the discharge of sterilant and steam from the chamber dilutes the sterilant out of the sterilizing chamber.

Referring to FIG. 1, this is accomplished by modulating the steam control valve 111 on and off relative to the selected pressure P-1. The vacuum level P1 is selected such that the steam entering the sterilizing chamber is superheated above the dew point on the surface and in the interstices of the load and will not exceed temperatures the materials can withstand without damage (e.g., searing or melting). On completion of a timed interval, e.g. 15 to 30 minutes, for the flush period 104 of FIG. 2, the sterilizing chamber environment is substantially entirely steam.

Next, the sterilizing chamber is pressurized with steam to a selected pressure P-2, such as 1.9 to 2.3 psia, as shown at 106. At this pressure, the steam enters the load and condenses inside the materials, but its temperature still does not exceed temperatures which would damage a load in the sterilizing chamber. High purity water condenses on the surface of the materials and the water extracts soluble sterilant gas from the materials.

Referring to FIG. 1, this is accomplished by closing the vacuum control valve 114 and opening the steam control valve 111 until the preselected pressure P-2 is attained upon which the steam valve is closed.

After a predetermined dwell period 106 of FIG. 2, the chamber is again evacuated to the vacuum level P1 shown at 107. The flush periods and subsequent pressure pulses are repeated until substantially virtually all of the sterilant is removed from the sterilizing chamber. On the last flush period 108, the sterilizing chamber is vented to atmospheric pressure with air in order to allow removal of the load (vent apparatus not shown). Although FIG. 2 shows a dwell period 106 for the higher pressure about equal to that of the vacuum flush period 104, the length of time for the higher pressure pulse can vary considerably depending on the the materials being sterilized. Thus some materials such as cotton fabrics, paper and metal articles, require no dwell time at the higher pressure, an instantaneous pulse being sufficient. Other substances, e.g., plastics benefit from substantial time at the higher pressure, e.g., up to 10 minutes. Hence, the duration of the higher pressure pulse can range, e.g. from about 0 to 10 minutes.

It has been found that during the sequence of steam flushing and pressure pulses, when the sterilant and steam contact the cold water used in the vacuum pump seal water, the steam condenses in the seal water and the sterilant gas passes on to the compressor 116. When the flow of sterilant from the sterilizing chamber decreases, the flow of sterilant from the vacuum pump to the compressor decreases proportionately and stops when all sterilant is removed from the sterilizer. Thus, all sterilant is flushed or diluted from the sterilizing chamber with the vacuum draws and steam flushes. Because the gases are selectively condensable (i.e., the water separated in the water seal pump and the sterilant liquefied in the condenser) most of the dilutent steam is removed from the effluent while the sterilant passing through the vacuum pump is collected.

While the preferred sequence for using a diluent to transport sterilant out of the sterilizing chamber and the load has been described, the sterilant can be removed from the sterilizing chamber and the load and be collected (although with some loss in efficiency) by using a low pressure steam flush alone, e.g., at 0.8 to 1.1 psia for extended periods of time, e.g. for 2 to 8 hours, as shown at 104 of FIG. 2 without a sequence of pressure pulses. Another possible procedure is to use fluctuating steam pressure pulses and evacuation for an extended period of time while controlling the steam pulse and the evacuation level between two pressure limits P-1 and P-2, but without dwell periods at each pressure limit. Best efficiency, however, is achieved with the preferred sequence which includes (a) sterilizing at elevated pressure, (b) evacuating the chamber to remove sterilant, (c) flushing the chamber with steam at vacuum pump pressure, (d) repressuring with steam, and repeating the sequence (c) and (d) at least once, then evacuating and finally purging the chamber with air at atmospheric pressure.

Variations and modifications in the herein described preferred embodiments of the invention within the scope of the invention will suggest themselves to those skilled in the art. Accordingly, the foregoing description should be taken as illustrative and not by way of limitation.

I claim:

1. A method for safely recovering a flammable chemical sterilant gas from a sterilizing chamber following the treatment of material within the chamber with said gas at an elevated pressure which comprises:

(a) reducing the pressure in said chamber, (b) flushing the chamber at the reduced pressure with a stream of substantially condensable, inert dilutant gas, (c) recovering from the chamber a discharge stream comprising said sterilant and said condensable dilutant, (d) subjecting said stream to conditions of temperature and pressure for causing said dilutant to condense but not the sterilant gas, thereby separating the dilutant from the sterilant gas, and thereafter (e) recovering the sterilant gas.

2. A method according to claim 1 wherein said elevated pressure is a superatmospheric pressure and the flushing of the chamber in step (b) is at subatmospheric pressure.

3. A method according to claim 1 wherein the sterilant gas is ethylene oxide and the condensable dilutent is steam.

4. A method according to claim 3 wherein steam is flowed through the chamber for a period of time sufficient to remove substantially all of the ethylene oxide from the chamber.

5. A method according to claim 4 wherein the elevated Pressure is above about 19 psia and the chamber is flushed with steam at a pressure from about 1 to 2 psia.

6. A method according to claim 3 wherein after flushing the chamber with steam, (a) the pressure in the chamber is raised to a level sufficient to condense steam on the load being sterilized and for a time sufficient to extract ethylene oxide from the load, (b) thereafter, steam is flowed through the chamber at a reduced pressure which is sufficiently low to vaporize the condensed steam and ethylene oxide and flush them from the chamber, and (c) the sequence of steps (a) and (b) is repeated until substantially all of the ethylene oxide is removed from the chamber.

7. A method according the claim 6 wherein the ethylene oxide gas after separation from the steam condensate is subjected to conditions of temperature and pressure causing it to liquefy.

8. A method of recovering a chemical sterilant gas from a sterilizing chamber which comprises flushing the chamber with a substantially condensable, insert dilutent gas and selectively condensing the effluent dilutent gas to separate the sterilant gas from the dilutant.

9. A method according to claim 8 wherein the sterilant gas is a flammable gas and the dilutent gas is steam.

10. A method according to claim 8 wherein the sterilant gas is ethylene oxide.

* * * * *